United States Patent
Bharat et al.

(10) Patent No.: US 11,786,318 B2
(45) Date of Patent: *Oct. 17, 2023

(54) INTELLIGENT REAL-TIME TOOL AND ANATOMY VISUALIZATION IN 3D IMAGING WORKFLOWS FOR INTERVENTIONAL PROCEDURES

(71) Applicant: KONINKLIJKE PHILIPS N.V., Eindhoven (NL)

(72) Inventors: Shyam Bharat, Arlington, MA (US); Ameet Kumar Jain, Boston, MA (US); Antonio Bonillas Vaca, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/693,755

(22) Filed: Mar. 14, 2022

(65) Prior Publication Data
US 2022/0192760 A1 Jun. 23, 2022

Related U.S. Application Data

(63) Continuation of application No. 15/324,095, filed as application No. PCT/IB2015/055320 on Jul. 14, 2015, now Pat. No. 11,298,192.
(Continued)

(51) Int. Cl.
*A61B 34/20* (2016.01)
*A61B 8/08* (2006.01)
(Continued)

(52) U.S. Cl.
CPC ............ *A61B 34/20* (2016.02); *A61B 8/0841* (2013.01); *A61B 8/12* (2013.01); *A61B 8/4254* (2013.01);
(Continued)

(58) Field of Classification Search
CPC ......... A61B 34/20; A61B 8/0841; A61B 8/12; A61B 8/4254; A61B 8/483; A61B 8/5261;
(Continued)

(56) References Cited

U.S. PATENT DOCUMENTS 4,407,294 A 10/1983 Vilkomerson
6,038,468 A 3/2000 Rex
(Continued)

FOREIGN PATENT DOCUMENTS

CN 101467896 A 7/2009
JP 3057442 B1 6/2000
(Continued)

*Primary Examiner* — Peter Luong

(57) ABSTRACT

A system for tracking an instrument includes two or more sensors (22) disposed along a length of an instrument and being spaced apart from adjacent sensors. An interpretation module (45) is configured to select and update an image slice from a three-dimensional image volume in accordance with positions of the two or more sensors. The three-dimensional image volume includes the positions two or more sensors with respect to a target in the volume. An image processing module (48) is configured to generate an overlay (80) indicating reference positions in the image slice. The reference positions include the positions of the two or more sensors and relative offsets from the image slice in a display to provide feedback for positioning and orienting the instrument.

20 Claims, 6 Drawing Sheets

Related U.S. Application Data

(60) Provisional application No. 62/025,481, filed on Jul. 16, 2014.

(51) Int. Cl.
    *A61B 8/12*     (2006.01)
    *A61B 8/00*     (2006.01)
    *A61B 10/02*     (2006.01)
    *A61B 90/00*     (2016.01)
    *A61B 34/10*     (2016.01)

(52) U.S. Cl.
    CPC ............ *A61B 8/483* (2013.01); *A61B 8/5261* (2013.01); *A61B 10/0241* (2013.01); *A61B 2034/107* (2016.02); *A61B 2034/2051* (2016.02); *A61B 2034/2063* (2016.02); *A61B 2090/364* (2016.02); *A61B 2090/3782* (2016.02); *A61B 2090/3786* (2016.02)

(58) Field of Classification Search
    CPC ........ A61B 10/0241; A61B 2034/2051; A61B 2034/2063; A61B 2090/364; A61B 2090/3782; A61B 2090/3786
    See application file for complete search history.

(56) References Cited

U.S. PATENT DOCUMENTS

| | | |
|---|---|---|
| 6,587,709 B2 | 7/2003 | Solf |
| 7,869,854 B2 | 1/2011 | Shachar |
| 8,290,303 B2 | 10/2012 | Washburn |
| 9,198,688 B2 | 12/2015 | Robinson |
| 10,434,278 B2 | 10/2019 | Dunbar |
| 2008/0186378 A1 | 8/2008 | Shen |
| 2008/0187245 A1 | 8/2008 | Habets |
| 2008/0291784 A1 | 11/2008 | Yamanaka |
| 2010/0022871 A1 | 1/2010 | De Beni |
| 2010/0217117 A1 | 8/2010 | Glossop |
| 2010/0268067 A1 | 10/2010 | Razzaque |
| 2010/0298705 A1 | 11/2010 | Pelizzier |
| 2012/0143055 A1 | 6/2012 | Ng |
| 2013/0197357 A1* | 8/2013 | Green .................. A61B 90/361 600/424 |
| 2013/0289393 A1 | 10/2013 | Kruecker |
| 2013/0317347 A1 | 11/2013 | Kwiat |
| 2014/0142425 A1 | 5/2014 | Razzaque |

FOREIGN PATENT DOCUMENTS

| | | |
|---|---|---|
| WO | 9729682 A1 | 8/1997 |
| WO | 9729709 A1 | 8/1997 |
| WO | 2012141914 A1 | 10/2012 |

* cited by examiner

INTELLIGENT REAL-TIME TOOL AND ANATOMY VISUALIZATION IN 3D IMAGING WORKFLOWS FOR INTERVENTIONAL PROCEDURES

CROSS-REFERENCE TO PRIOR APPLICATIONS

This application is a Continuation of application Ser. No. 15/324,095, filed Jan. 5, 2017, which is the U.S. National Phase application under 35 U.S.C. § 371 of International Application No. PCT/IB2015/055320, filed on Jul. 14, 2015, which claims the benefit of U.S. Provisional Patent Application Ser. No. 62/025,481, filed Jul. 16, 2014. These applications are hereby incorporated by reference herein.

RELATED APPLICATION INFORMATION

This application claims priority to provisional application Ser. No. 62/025,481, filed on Jul. 16, 2014, incorporated herein by reference in its entirety.

BACKGROUND

Technical Field

This disclosure relates to medical instruments and more particularly to a system and method to track a needle under ultrasound guidance with tool and anatomical visualization.

Description of the Related Art

A biopsy can be described as a minimally invasive procedure where a sample of tissue is obtained for ex vivo pathologic analysis. Typically, a biopsy device (or biopsy gun) can comprise an inner stylet and outer hollow cannula, both of which can be attached to the biopsy gun handle. In many instances, the biopsy gun can be a disposable device. A typical biopsy device can be positioned in tissue under some form of image guidance (typically ultrasound (US)) and then 'fired'. The act of firing generally first deploys the inner stylet and then the outer cannula in quick succession, thus capturing a tissue sample in the slot of the inner stylet. The actual location of the biopsy sample can be offset from the resting position of the biopsy device prior to firing. Proper positioning of the biopsy gun and needle is an important factor in retrieving tissue from a correct location.

SUMMARY

In accordance with the present principles, a system for tracking an instrument includes two or more sensors disposed along a length of an instrument and being spaced apart from adjacent sensors. An interpretation module is configured to select and update an image slice from a three-dimensional image volume in accordance with positions of the two or more sensors. The three-dimensional image volume includes the positions two or more sensors with respect to a target in the volume. An image processing module is configured to generate an overlay indicating reference positions in the image slice. The reference positions include the positions of the two or more sensors and relative offsets from the image slice in a display to provide feedback for positioning and orienting the instrument.

Another system for tracking an instrument includes two or more sensors disposed along a length of an instrument and being spaced apart from adjacent sensors. An imaging system is configured to image positions of the two or more sensors in a plurality of image slices. An interpretation module is configured to select and update an image slice from the plurality of image slices corresponding to a plane in a three-dimensional image. The interpretation module selects the image slice based upon locations of reference positions. The reference positions include the positions of at least the two or more sensors and a target. An image processing module is configured to generate an overlay indicating the reference positions in the image slice, the reference positions including the positions of the two or more sensors and relative offsets from the image slice in a display to provide feedback for positioning and orienting the instrument.

A method for tracking a medical instrument includes detecting positions of two or more sensors disposed along a length of an instrument and being spaced apart from adjacent sensors; selecting and updating an image slice from a three-dimensional volume, the three-dimensional volume including the two or more sensors with respect to a target in the volume; and generating an overlay indicating reference positions in the image slice, the reference positions including positions of two or more sensors and relative offsets from the image slice in a display; and positioning and orienting the instrument in accordance with feedback from the overlay including positions of the two or more sensors and the relative offsets from the image slice.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
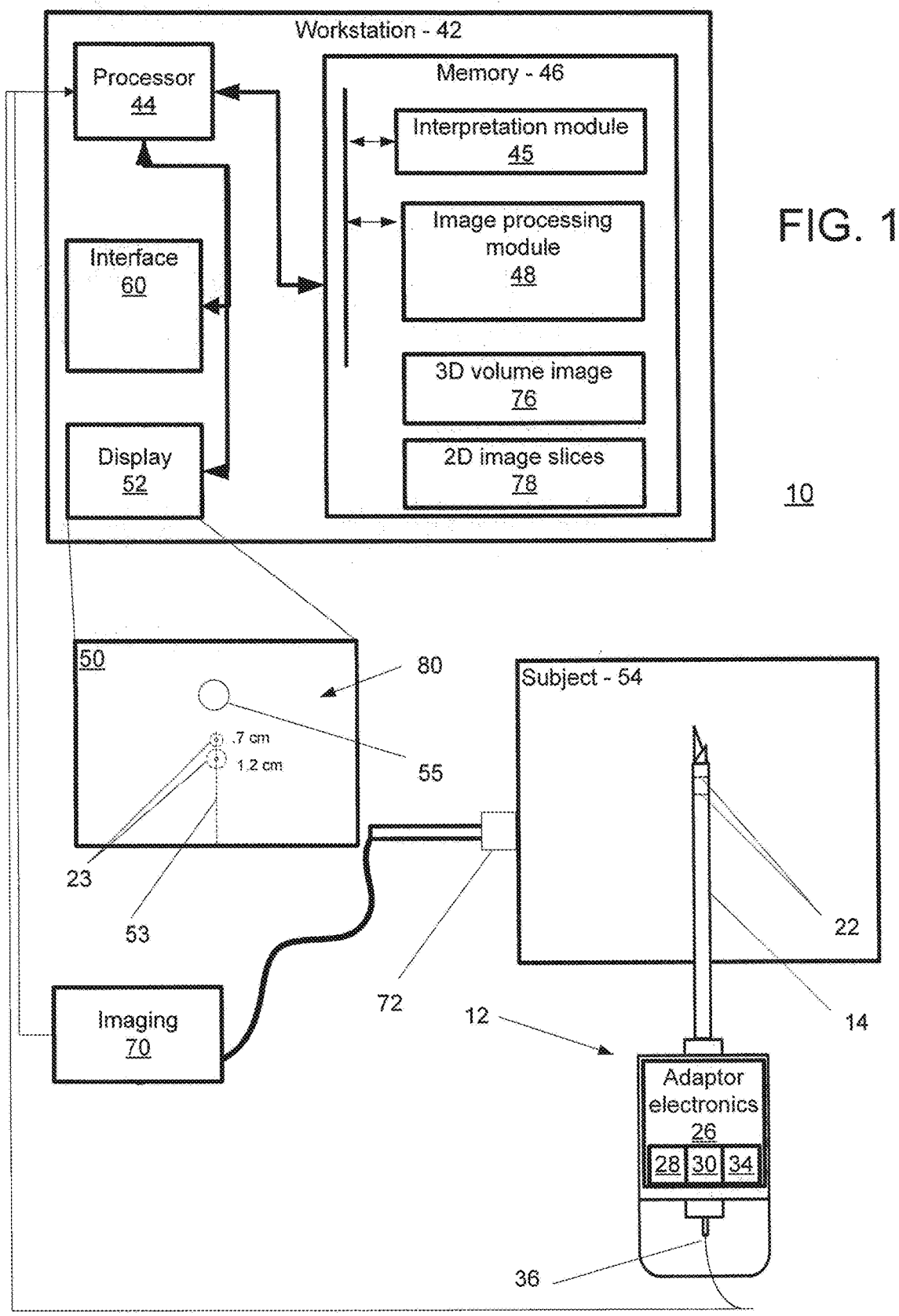
FIG. 1 is a schematic block/flow diagram showing a system for tracking a medical device using 2D slices in accordance with one embodiment.

In accordance with the present principles, embodiments are provided that interpret tracked three-dimensional (3D) positions and orientations of a medical instrument (e.g., a biopsy tool) with respect to a current image or image slice (e.g., transrectal ultrasound (TRUS), magnetic resonance images (MRI), etc.), choose and re-render two-dimensional (2D) images or image slices to display, so they include real-time tracked tool position(s) and overlay tool representations on appropriate images or image slices (e.g., an oblique magnetic resonance (MR) slice).

Targeted prostate biopsy procedures may be performed under real-time 2D TRUS imaging, after an intraprocedurally-acquired 3D TRUS image set is registered to a preprocedure 3D MR image set. Live 3D TRUS imaging is attractive because the prostate can potentially be imaged without moving (or by minimally moving) the TRUS probe, leading to more accurate TRUS-MR registration. However, in such a 3D workflow, identifying and displaying the biopsy tool in a user-friendly and intuitive manner is a challenge.

The present principles employ ultrasound (US) tracking technology (e.g., 'InSitu'), which is configured to work in a 3D US environment. Since the 3D position of the sensor is known, it is possible to estimate the location of that sensor with respect to a given 2D image plane. This is a very useful feature since even in 3D workflows guidance is often performed using 2D image renderings. A method for intelligent real-time visualization of a medical tool (e.g., a biopsy needle) and the surrounding anatomy is provided. This aids in the adoption of a 3D workflow for interventional procedures, by enabling the identification and display of the biopsy tool in a user-friendly and intuitive manner.

In one embodiment, a real-time 3D tracked position of the tracking sensor(s) is employed to quantitatively estimate the sensor's location with respect to a current 2D imaging plane. Each sensor may be represented by a circle or other shape of varying size (the larger the size, the further it is from the current image plane (or vice versa)), along with its distance from the current image plane. In another embodiment, the displayed 2D TRUS image is re-rendered in real-time (from the live 3D image) to include a current pose of the biopsy tool. This provides a real-time view of the anatomy in the vicinity of the biopsy tool, which can be especially useful during insertion of the tool. In another embodiment, the known TRUS-MR registration is employed to continuously update and display the 2D MR slice that shows the biopsy tool. This provides added value, since it is more intuitive to navigate the biopsy tool in the MR image, which provides richer soft tissue information. The biopsy tool is also indicated.

It should be understood that the present invention will be described in terms of medical instruments; however, the teachings of the present invention are much broader and are applicable to any trackable instruments. In some embodiments, the present principles are employed in tracking or analyzing complex biological or mechanical systems. In particular, the present principles are applicable to internal tracking procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Further, it should be understood that any new computer-readable medium which may hereafter be developed should also be considered as computer-readable medium as may be used or referred to in accordance with exemplary embodiments of the present invention and disclosure.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C).

This may be extended, as readily apparent by one of ordinary skill in this and related arts, for as many items listed.

It will also be understood that when an element such as, e.g., a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, an illustrative tracking or biopsy system 10 is shown in accordance with one embodiment. The system 10 includes a biopsy gun or other instrument 12 configured for tracking. The instrument 12 may include a biopsy needle 14 having an inner stylet 16 disposed within an outer cannula 18. The needle 14 includes one or more tracking sensors 22 associated with it. The tracking sensors 22 may include ultrasonic sensors although other types of sensors may be employed for tracking the needle 14.

In one embodiment, adaptor electronics 26 may include noise cancellation modules 28 (software and/or hardware), amplifiers 30 and any another signal processing modules 34 needed to process received signals from sensors 22.

The sensors 22 may include one or more ultrasound trackers. The sensors 22 may be disposable or non-disposable. In one embodiment, the ultrasound trackers for sensors 22 may include PZT, PVDF, or other piezoelectric element disposed between conductive plates or layers. A sensor cable 36 can be provided as an output to a workstation or other device, although wireless interfaces are also contemplated.

The one or more ultrasound trackers or sensors 22 can be tracked using InSitu technology. If at least two sensors 22 are employed, the orientation of the needle 14 can be estimated. Therefore, the biopsy location coordinates can be computed prior to firing the needle 14.

InSitu technology estimates the position of a passive ultrasound sensor (e.g., PZT, PVDF, copolymer or other piezoelectric material) in a field of view (FOV) of a diagnostic B-mode image by analyzing the signal received by the sensor as the beams of the imaging probe sweep the FOV. Time-of-flight measurements provide the axial/radial distance of the PZT sensor from the imaging array, while amplitude measurements and knowledge of the beam firing sequence provide the lateral/angular position of the sensor. The sensor passively listens to the ultrasound waves impinging on it as the imaging probe's beams sweep the field of view. Analysis of these signals yields the position of the sensor on the tool in the frame of reference of the ultrasound image. The position can then be overlaid on the ultrasound image for enhanced tool visualization, and the positions and their histories can be logged for tracking, segmentation, and other applications.

When used with 3D transducers (e.g., 2D matrix arrays), the elevational position of the sensor(s) 22 can also be obtained in a similar manner. Therefore, the 3D position of the sensor 22 can be estimated in real-time, provided it is present within the FOV of the imaging transducer. Since the 3D position of the sensor 22 can be ascertained, it is also possible to estimate the location of that sensor 22 with respect to a given 2D image plane.

Targeted prostate biopsy procedures are currently performed under real-time 2D transrectal US (TRUS), after an intraprocedurally-acquired 3D TRUS image set is registered to a pre-procedural 3D MR image set. Live 3D TRUS imaging is attractive because an organ can potentially be imaged without moving (or by minimally moving) an imaging probe, leading to more accurate registration (e.g., US to MR). However, in such a 3D workflow, identifying and displaying the biopsy tool in a user-friendly and intuitive manner is a challenge.

The InSitu US tracking technology can be adapted to work in a 3D US environment. Since the 3D position of the sensor 22 is known, it is possible to estimate the location of that sensor 22 with respect to a given 2D image plane. This is a very useful feature since even in 3D workflows guidance is often performed using 2D image renderings. Intelligent real-time visualization of the instrument 12 and the surrounding anatomy can be provided in accordance with the present principles to enable clinicians to avail the advantages of a 3D workflow by providing a solution to the data interpretation problems associated with the 3D workflow.

The system 10 may work in conjunction with or be integrated in a workstation or console 42 from which a procedure is supervised and/or managed. Workstation 42 preferably includes one or more processors 44 and memory 46 for storing programs and applications. Memory 46 may store an interpretation module 45 configured to interpret feedback signals from sensors 22. Interpretation module 45 is configured to employ the signal feedback (and any other feedback, e.g., electromagnetic (EM) tracking) to reconstruct position and orientation of the needle 14 or other medical device or instrument. The other medical devices may include a catheter, a guidewire, a probe, an endoscope, a robot, an electrode, a filter device, a balloon device, or other medical component, etc.

In one embodiment, workstation 42 includes an image processing module 48 configured to receive feedback from the sensors 22 and further process the information to determine position and orientation of the sensors 22 within a volume (subject) 54. An image 50 of the space or volume 54 can be generated and displayed on a display device 52 that indicates the position and orientation of a representation 53 of the needle 14 (and other components) in a live image.

Interpretation module 45 can also be configured to determine an estimated position/target 55 of where a biopsy sample will be taken in the subject 54. The interpretation module 45 may convey this information to the image processing module 48 to generate an image showing a location of the estimated position to assist a user. The image may include a line or other shape to provide a visual indicator (53).

Workstation 42 includes the display 52 for viewing internal images of a subject (patient) or volume 54 and may include the image as an overlay or other rendering having a representation 23 of the sensors 22, the representation 53 of the needle 14, representation of a target 55, anatomical features, etc. Display 52 may also permit a user to interact with the workstation 42 and its components and functions, or any other element within the system. This is further facilitated by an interface 60 which may include a keyboard, mouse, a joystick, a haptic device, or any other peripheral or control to permit user feedback from and interaction with the workstation 42.

An imaging system 70 (e.g., real-time) is provided for imaging the needle 14 or other instrument for guidance and positioning. In one embodiment, the imaging system 70 includes an ultrasound imaging system, which employs an imaging probe 72. The imaging probe 72 provides ultrasonic energy, which is received by the sensors 22. The sensors 22 are electrically connected (wirelessly or by employing wires, not shown) to the adaptor electronics 26 for signal processing and amplification. The adaptor electronics 26 may in turn be connected to the workstation 42 where the interpretation module 45 further processes the signals, registers the needle 14 or other instrument (and other components) to the images collected by the imaging system 70. While the imaging system 70 is described as an ultrasound imaging system 70, other imaging technologies may be employed.

The interpretation module 45 may be employed to interpret a tracked 3D image volume 76 to determine a position and orientation of the biopsy tool or needle 14 with respect to a current image slice or image 78. The interpretation module 45 selects image slices 78, e.g., 2D TRUS/MR image slices to display, so it contains the real-time tracked tool position(s). The interpretation module 45 employs a field of view that includes all or some trackable features (e.g., sensor position, instrument position, biopsy/target location, etc.). Using the positions (e.g., depths), the interpretation module 45 selects an image slice (50) that best defines the relationship between the sensors 22 on the needle 14 and the biopsy location. The interpretation module 45 may select a plane where all trackable positions are present or may select another plane based upon criteria stored in the interpretation module 45 that best shows the relationship. The criteria may include an angle for best viewing internal organs, best viewing the target, best viewing the needle or other instrument, etc. The biopsy tool or needle 14 may be overlaid on the appropriate slice (e.g., TRUS/MR slice, oblique MR slice) to be viewed on the display 52. An overlay 80 may be generated as a representation of the needle 14, an image of the needle, etc.

Figure 2:
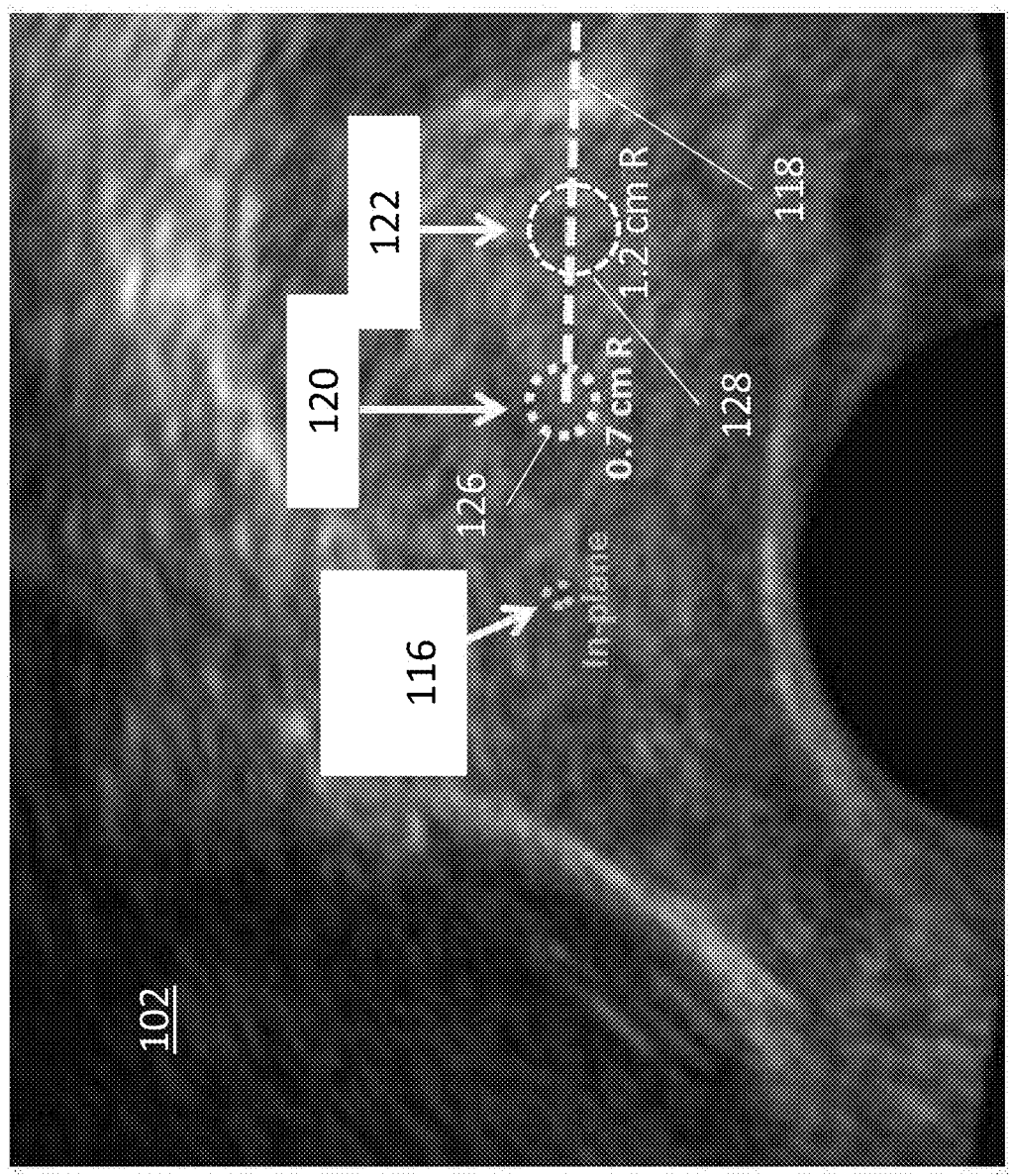
FIG. 2 is an image having an overlay indicating sensor positions and relative offsets in accordance with one embodiment.

Referring to FIG. 2, an illustrative visualization of a biopsy tool with respect to a current 2D TRUS image 102 is shown. Note that in a 3D use case, which is being addressed; this 2D image 102 is a plane formed by a subset of elements in a 3D probe. This example is for a transperineal biopsy procedure. The TRUS image 102 is a sagittal view of a prostate. A biopsy tool or needle 118 enters through the perineum, on a right side of the image. The tool 118 is equipped with two sensors 120 and 122 (e.g., for InSitu tracking). The size of a circle 126 and 128 indicates a distance of that sensor 120, 122, respectively, from a displayed 2D image plane. Note that, in this illustration, sensor 122 is out-of-plane by 1.2 cm and sensor 120 is out-of-plane by 0.7 cm. Note also that a biopsy location 116 is estimated to be in a current image plane (in-plane). Thus, the present principles enable identification of the biopsy location 116 in a given image plane even if the tool itself is not in the image plane. A dotted line indicates an estimated biopsy tool shaft 118 (projection in the current image plane).

The real-time 3D tracked position of the sensor(s) 120, 122 is employed to quantitatively estimate their location with respect to the current 2D imaging plane (e.g., the plane of the page) of image 102. Each sensor 120, 122 can be represented by a circle of varying size (e.g., larger the size, further it is from the current image plane), along with its distance from the current image plane. Other shapes or information may also be displayed. Since the sensor position is computed in 3 dimensions, the absolute distance from the current plane can be calculated.

For a transperineal biopsy procedure, the 2D TRUS image 102 (sagittal view of the prostate) provides a plane formed by a subset of elements in a 3D probe. The biopsy tool 118 and its two sensors 120, 122 (connected thereto) enter through the perineum, on the right. It should be understood that more than two sensors may be employed. The sensors 120, 122 are located using ultrasound feedback; the signals are employed to locate the sensors 120, 122 in image space. The positions of the sensors 120, 122 are interpreted by the interpretation module 45 (FIG. 1) and shapes, such as circles 126, 128 are generated to indicate position of the sensors 120, 122 relative to an imaging plane. The size of the circle 126, 128, e.g., indicates the distance of that sensor from the displayed 2D image plane, e.g., sensor 122 is out-of-plane (in the L-R direction) by 1.2 cm and sensor 120 is out-of-plane by 0.7 cm. The projected biopsy sample location is estimated to be in the current image plane; thus, the method enables identification of the biopsy location in a given image plane even if the tool itself is not in that image plane. While this embodiment is illustrated here for a transperineal biopsy, the present principles are applicable to other procedures as well, e.g., transrectal biopsy, transperineal or transrectal therapy (and other interventional procedures performed under 3D US image guidance). Also, while two sensors have been indicated, more than two sensors are contemplated. One sensor is also a possibility using other data. With one sensor, only position estimation may be accomplished when using only the sensor data, since orientation of the tool cannot be determined with just one sensor. In the event that a template/grid is utilized (and registered to the 3D image), the grid entry point may be combined with the estimated sensor location to estimate an orientation of the tool.

Figure 3:
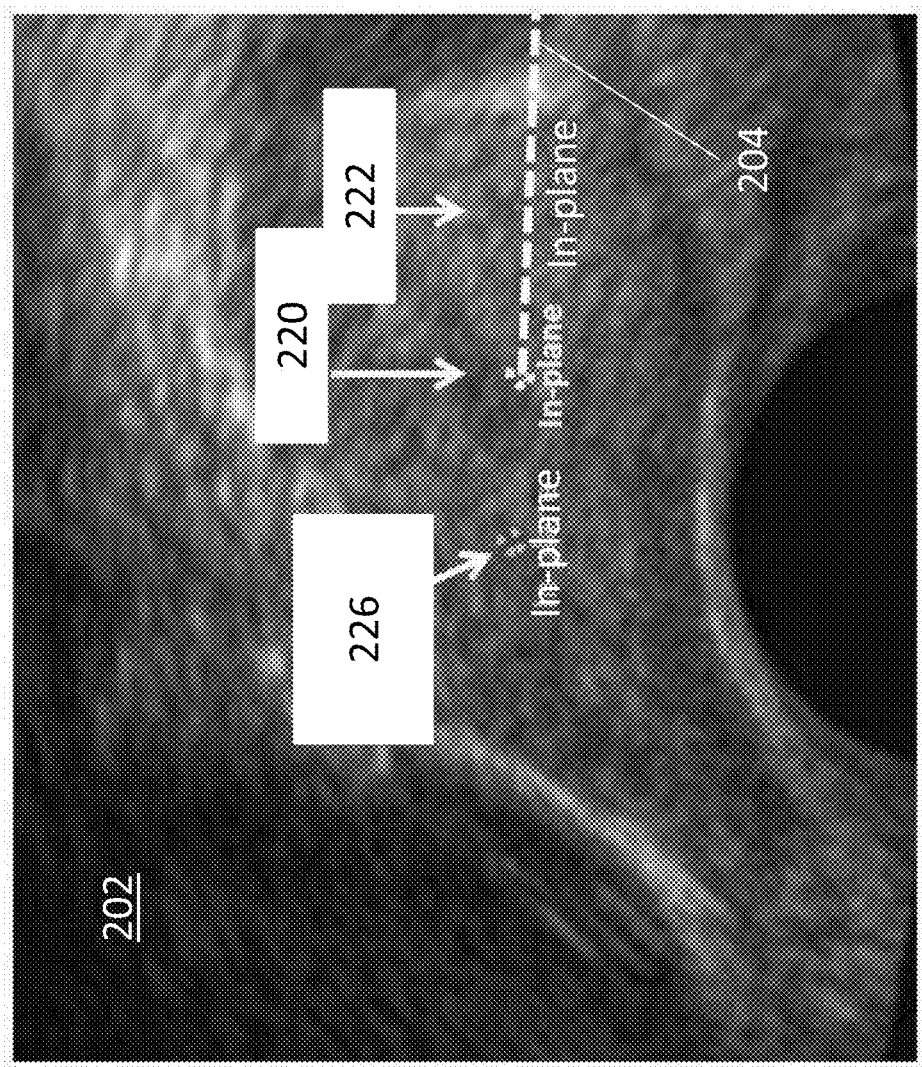
FIG. 3 is an image having in-plane reference positions indicated in an overlay in accordance with one embodiment.

Referring to FIG. 3, a 2D US image 202 includes a biopsy tool shaft 204 with two sensors 220, 222 and an estimated biopsy location 226 all in an image plane (plane of the paper). The displayed 2D TRUS image 202 is re-rendered in real-time (from the live 3D image) to coincide with a current position and pose of the biopsy tool shaft 204. As the tool 204 is advanced, the 2D image 202 on the screen is updated, by changing the selection of the subset of elements of the 3D probe array. Note that theoretically there are infinite planes that can contain the biopsy tool 204 (which is essentially a line). However, using the elements of the 3D probe array, such a plane would be unique. In other words, the in-plane positions of two or three reference points are employed to select the view plane. This feature provides a real-time view of the anatomy in the vicinity of the biopsy tool, which can be especially useful during insertion of the tool 204.

Figure 4:
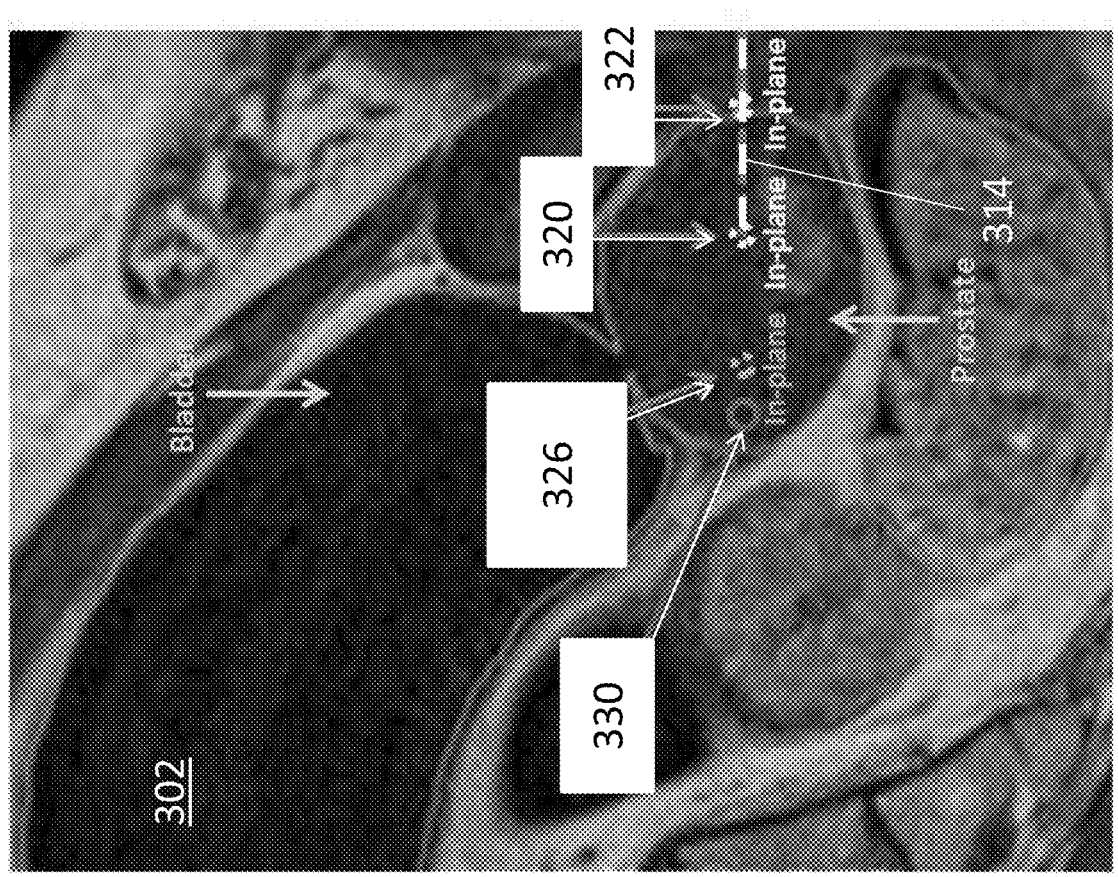
FIG. 4 is an image having an overlay indicating sensor positions, estimated biopsy location and a biopsy target position in accordance with one embodiment.

Referring to FIG. 4, a 2D MR image 302 is rendered to include a biopsy tool shaft 314. Note that both sensors 320, 322 and an estimated biopsy location 326 are all in the image plane. Note also the greater soft tissue contrast in the MR image 302, makes navigation easier. The known TRUS-MR registration is used to continuously update and display the 2D MR slice that includes the biopsy tool 314. As the tool 314 is advanced, the 2D MR image 302 on the screen is updated. This provides added value, since it is more intuitive to navigate the biopsy tool 314 in the MR image 302, which provides richer soft tissue information. If local biopsy targets are delineated in the MR image 302, the method enables tool guidance to an MR biopsy target 330 (the intended location) in a more accurate and user-friendly manner. A dotted circle may be employed to indicate the estimated location 326 from which the biopsy will be taken, if the biopsy needle is fired from a current location.

In accordance with the present embodiments, live 3D TRUS imaging is provided. In such a case, the prostate can potentially be imaged without moving (or by minimally moving) a TRUS probe, leading to more accurate TRUS-MR registration. This aids in the adoption of a 3D workflow for interventional procedures, by enabling the identification and display of the biopsy tool in a user-friendly and intuitive manner.

The use of ultrasound tracking technology (InSitu) can be utilized to more accurately estimate a true location of the biopsy sample. For example, InSitu technology can be used to estimate the position of a passive ultrasound sensor or sensors (e.g., PZT, PVDF, copolymer or other piezoelectric material) in a field of view (FOV) of a diagnostic B-mode image by analyzing a signal received by a sensor as beams of the imaging probe sweep the FOV. Time-of-flight measurements can be used to provide the axial/radial distance of the sensor(s) (FIG. 1) from the imaging array, while amplitude measurements and knowledge of the beam firing sequence can be used to provide (or determine) the lateral/angular position of the sensor. When used with 3D transducers (e.g., 2D matrix arrays) (US imaging probe), the elevational position of the sensor can also be obtained in a similar manner. Therefore, the 3D position of the sensor can be estimated in real-time, provided it is present within the FOV of the imaging transducer.

The sensors passively listen to the ultrasound waves impinging on them as the imaging probe's beams sweep the field of view. Analysis of these signals yields the position of the sensors in the frame of reference of the ultrasound image. The position can then be overlaid on an ultrasound image for enhanced visualization, and the positions and their histories can be logged for tracking, segmentation, and other applications. The image slice where two or more points or reference exists may be selected for visualization to further improve use. When used with 3D transducers (e.g., 2D matrix arrays), the elevational position of the sensor can also be obtained in a similar manner. Therefore, the 3D position of the sensor can be estimated in real-time, provided it is present within the FOV of the imaging transducer. Since the 3D position of the sensor can be ascertained, it is also possible to estimate the location of that sensor with respect to a given 2D image plane, for example.

Figure 5:
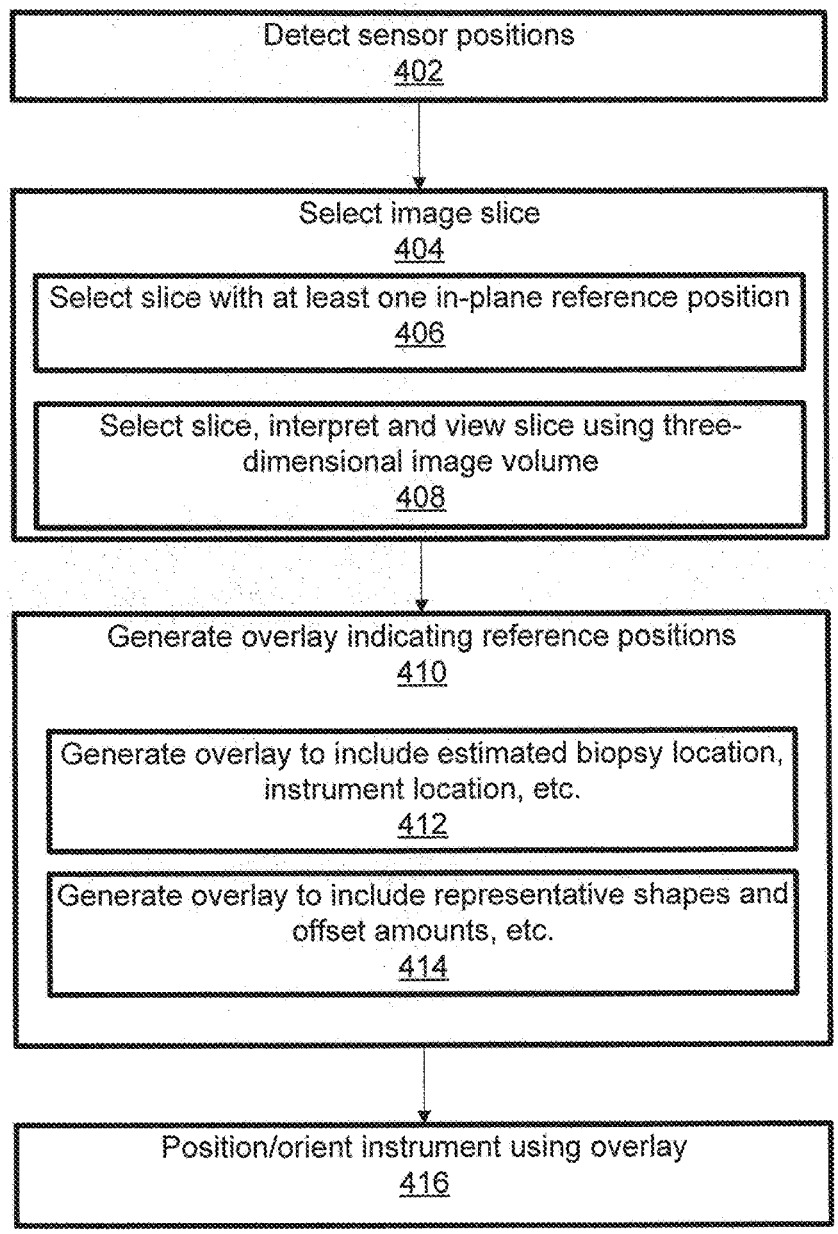
FIG. 5 is a flow diagram showing a method for tracking a medical instrument in accordance with illustrative embodiments.

Referring to FIG. 5, a method for tracking a medical instrument is illustratively shown. In block 402, positions of two or more sensors disposed along a length of an instrument are detected. The sensors are preferably spaced apart from adjacent sensors to provide orientation information as well as position of the instrument. In block 404, an image slice is selected and updated from a plurality of image slices. The selected image slice may be selected in accordance with reference positions. The relative positions may be tracked in a three-dimensional volume, which is interpreted to define a useful image slice. For example, the useful image slice may include the two or more sensors with respect to a target in the three-dimensional volume. The image slices are registered with the three dimensional volume. The image slices are updated in accordance with sensor movement. In this way, the image can be updated without moving the imaging probe.

In block 406, the image slice is selected to include at least one in-plane reference position (e.g., sensor position, instrument position, target position, etc.). In block 408, the image slice is selected using the three-dimensional volume. The three-dimensional (3D) positions and orientations of the instrument may be tracked and interpreted to determine a slice that includes, e.g., the two or more sensors with respect to a target using a real-time imaging system. The image slice from a three-dimensional volume may also be registered and interpreted using images from the tracked three-dimensional (3D) positions and orientations of the instrument, which may include the representations of the two or more sensors with respect to a current image slice gathered using the real-time imaging system. In addition, the positions of the two or more sensors in an image may be viewed with registered images from a second complementary imaging modality.

In block 410, an overlay is generated indicating the reference positions in the image slice. The reference positions may include the two or more sensors and relative offsets from the image slice in a display. In block 412, the overlay is generated to represent one or more of: an estimated biopsy location and the instrument location. In block 414, the overlay is generated to represent at least one of a shape and/or an offset distance for each reference position, wherein the shape may be proportionally sized relative to a magnitude of the offset distance. In block 416, the instrument is positioned and oriented in accordance with feedback from the overlay including positions of the two or more sensors and the relative offsets from the image slice.

Figure 6:
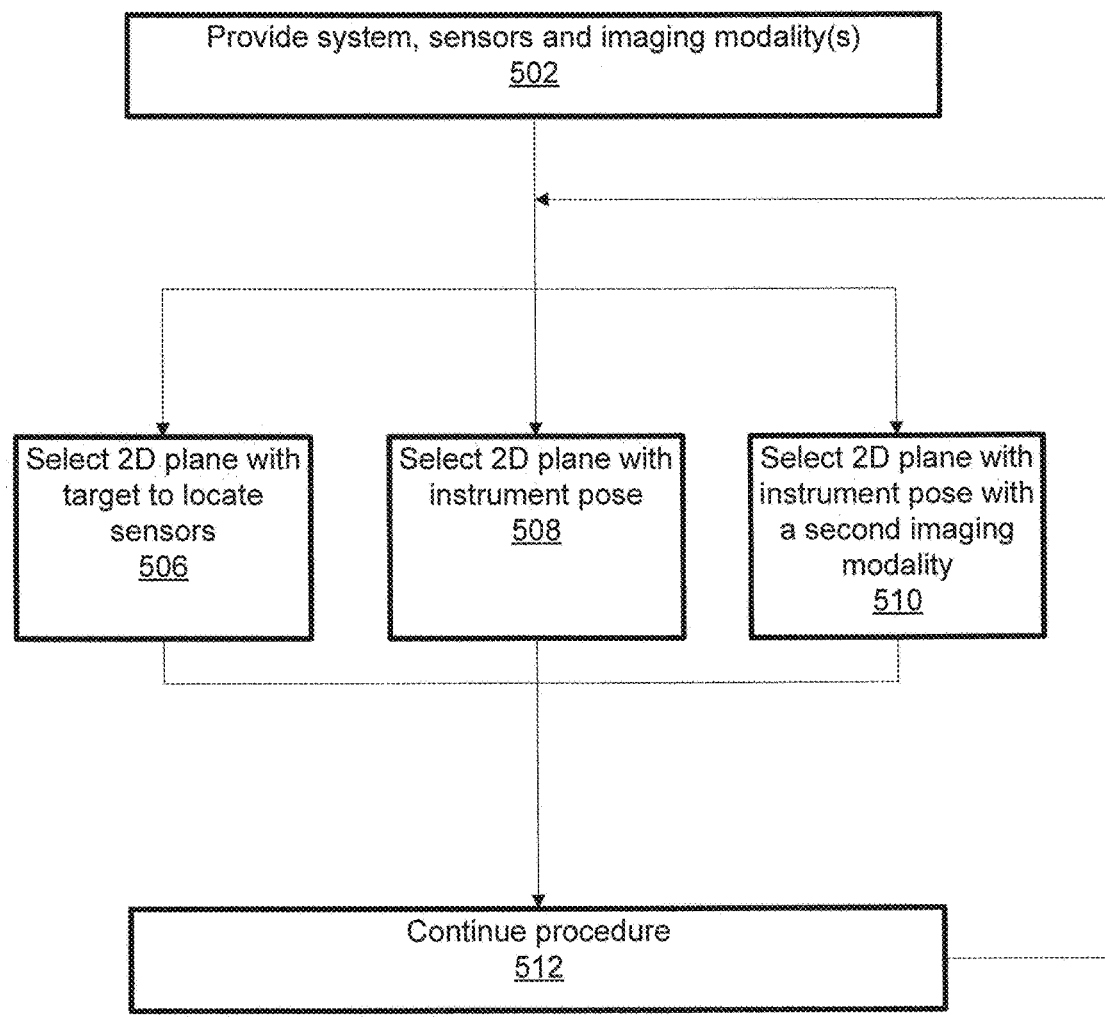
FIG. 6 is a flow diagram showing a method for selecting a perspective or utility operation for tracking a medical instrument in accordance with illustrative embodiments.

Referring to FIG. 6, a method for selecting a perspective for tool and anatomy visualization in imaging workflows for interventional procedures a medical instrument is illustratively shown. In block 502, a system in accordance with the present principles is provided. A first imaging modality (e.g., a real-time imaging system, e.g., ultrasound, x-ray, etc.) is employed to obtain 2D images of a volume, a second complementary modality (e.g., MRI, CT, PET, etc.) may also be employed to register its images to the first modality to provide enhancements to the image display. A medical instrument, e.g., a needle, is tracked using two or more sensors disposed on the instrument. In block 504, the instrument is positioned within the volume. At any time during a procedure one or more of the following blocks 506, 508 and/or 510 may be performed to improve perspective and provide a more user-friendly visual interaction.

In block 506, a user (clinician) selects a 2D plane that includes a biopsy target and certain areas of the anatomy, without necessarily including the instrument. The intent in this case (sensor tracking) is to provide information on how far each sensor (and therefore, the instrument) is from the selected 2D image plane. This may permit the user to confirm that the instrument is sufficiently far from any sensitive areas ("no fly zones" such as, e.g., the urethra) in the path to the target. An example of the 2D image plane selected in this embodiment could be a conventional sagittal image plane imaged by currently available 2D TRUS probes.

In block 508, the user may wish to view the 2D plane that includes a pose of the instrument, to view the anatomy currently surrounding the instrument (instrument tracking). An example of such a 2D image plane could be an oblique plane that includes the instrument pose (depending on the pose achieved, this could differ from a truly sagittal plane).

In block 510, the user may wish to view the instrument in a selected plane but employing information from a secondary imaging source. The instrument plane is selected similarly to that described in block 510, except that the 2D image plane visualized is from a registered second complementary imaging modality (e.g., MRI, PET, PET-CT, etc.). This permits the benefits of US-based device tracking to be combined with superior anatomical information available from the second imaging modality.

In block 512, the procedure continues. At any time, the user may select to employ any one of the blocks 506, 508 and/or 510 to assist in performing the procedure. Note that the functions of blocks 506, 508 and/or 510 may be called out and performed at any point in the method depicted in FIG. 5. Each of blocks 506, 508 and/or 510 can be carried out at any time during the interventional procedure, depending on clinical need.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for intelligent real-time tool and anatomy visualization in 3D imaging workflows for interventional procedures (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for tracking an instrument, the system comprising:
a sensor disposed along a length of the instrument;
an interpretation processor configured to select and update an image slice from a three-dimensional image volume based on position of the sensor, the three-dimensional image volume including the position of the sensor with respect to a target in the three-dimensional image volume, wherein the interpretation processor is configured to select the image slice to include at least one in-plane reference position; and
an image processor configured to generate, in a display, an overlay indicating reference positions in the image slice, the reference positions including the position of the sensor and relative offset measurements for the sensor from the image slice to provide feedback for positioning the instrument.

2. The system of claim 1, wherein the instrument includes a biopsy needle, and the image processor is further configured to generate an overlay for an estimated biopsy location.

3. The system of claim 1, wherein the image processor is further configured to generate an overlay for the instrument or position of the instrument.

4. The system of claim 1, wherein:
the at least one in-plane reference position comprises at least one of: an in-plane sensor position, an in-plane instrument position, and an in-plane target position;
the sensor is an ultrasound sensor; and
the interpretation processor is further configured to analyze ultrasound signals received by the ultrasound sensor as ultrasound beams sweep a field of view and to determine a position of the ultrasound sensor respective the field of view.

5. The system of claim 1, wherein the interpretation processor is further configured to select the image slice to include the at least one in-plane reference position.

6. The system of claim 1, wherein, for each of the reference positions, the overlay indicates a shape, an offset distance, or both the shape and the offset distance.

7. The system of claim 6, wherein the shape is proportionally sized relative to a magnitude of the offset distance.

8. The system of claim 1, wherein the reference positions further include at least one of: a target of a medical device, an estimated position of the medical device, and a representation of the medical device.

9. The system of claim 1, further comprising:
a second imaging system configured to generate two-dimensional (2D) images in real-time, and
a first imaging system configured to generate three-dimensional (3D) images of the three-dimensional image volume and register the 3D images with the 2D images in a field of view that includes the sensor.

10. The system of claim 1, further comprising:
an imaging system configured to provide the image slice including the position of the sensor.

11. The system of claim 10, wherein:
the imaging system includes a transrectal ultrasound probe and the instrument includes a biopsy needle, and
the image processor is further configured to generate an overlay for an estimated biopsy location.

12. A method for tracking an instrument, the method comprising:
detecting a position of a sensor disposed along a length of the instrument;
selecting and updating an image slice from a three-dimensional image volume based on the position of the sensor, the three-dimensional image volume including the position of the sensor with respect to a target in the three-dimensional image volume, wherein the selecting includes selection of the image slice to include at least one in-plane reference position;
generating, in a display, an overlay indicating reference positions in the image slice, the reference positions including the position of the sensor and relative offset measurements for the sensor from the image slice; and
positioning the instrument in accordance with feedback from the overlay.

13. The method of claim 12, further comprising:
generating the overlay to represent an estimated biopsy location, an instrument location, or both the estimated biopsy location and the instrument location.

14. The method of claim 12, further comprising:
for each of the reference positions, generating the overlay to represent a shape, an offset distance, or both the shape and the offset distance, wherein the shape is proportionally sized relative to a magnitude of the offset distance.

15. The method of claim 12, wherein selecting and updating the image slice includes interpreting a tracked three-dimensional position of the instrument with respect to a current image slice gathered using a real-time imaging system.

16. The method of claim 12, wherein selecting and updating the image slice includes viewing the position of the sensor in an image that includes a second complementary imaging modality image.

17. A non-transitory computer readable medium having instructions encoded thereon which, when executed by a processor, cause the processor to:

select and update an image slice from a three-dimensional image volume based on a position of a sensor (i) disposed along a length of an instrument and (ii) configured to be tracked during a medical procedure, the three-dimensional image volume including the position of the sensor with respect to a target in the three-dimensional image volume, wherein the image slice is selected to include at least one in-plane reference position; and generate, in a display, an overlay that indicates reference positions in the image slice to provide feedback for positioning the instrument, the reference positions including the position of the sensor and relative offset measurements for the sensor from the image slice.

18. The non-transitory computer readable medium of claim 17, wherein the instrument includes a biopsy needle, and wherein the instructions further comprise instructions which, when executed by the processor, cause the processor to generate an overlay for an estimated biopsy location.

19. The non-transitory computer readable medium of claim 17, wherein the instructions further comprise instructions which, when executed by the processor, cause the processor to generate the overlay for the instrument and to select the image slice to include the at least one in-plane reference position.

20. The non-transitory computer readable medium of claim 17, wherein:

the at least one in-plane reference position comprises at least one of: an in-plane sensor position, an in-plane instrument position, and an in-plane target position;

the sensor is an ultrasound sensor; and the instructions further comprise instructions which, when executed by the processor, cause the processor to analyze ultrasound signals received by the ultrasound sensor as ultrasound beams sweep a field of view and to determine a position of the ultrasound sensor respective the field of view.

\* \* \* \* \*